United States Patent [19]

Nevyas et al.

[11] Patent Number: 4,955,883
[45] Date of Patent: Sep. 11, 1990

[54] GLAUCOMA NEEDLE WITH A THERMAL HEAT BAND

[75] Inventors: Herbert J. Nevyas, Narberth; Michael H. Loughnane, Philadelphia, both of Pa.

[73] Assignee: Diversatronics, Broomall, Pa.

[21] Appl. No.: 237,798

[22] Filed: Aug. 29, 1988

[51] Int. Cl.$^5$ .............................................. A61B 17/36
[52] U.S. Cl. ...................................... 606/28; 128/401
[58] Field of Search ...................... 128/303.1, 305, 401; 219/229, 233, 236, 237; 606/27–31, 49

[56] References Cited

U.S. PATENT DOCUMENTS

| | | | |
|---|---|---|---|
| 1,355,932 | 10/1920 | Walter | 128/401 |
| 1,677,642 | 7/1928 | Kirk | 128/401 |
| 2,069,284 | 2/1937 | Solomon | 128/401 |
| 3,698,394 | 10/1972 | Piper et al. | 128/303.1 |
| 3,851,145 | 11/1974 | Fukanaga | 219/229 |
| 4,122,850 | 10/1978 | Bacalo | 219/229 |
| 4,185,633 | 1/1980 | Prozorov et al. | 128/305 |
| 4,830,260 | 5/1989 | Kent | 219/229 |

FOREIGN PATENT DOCUMENTS

| | | | |
|---|---|---|---|
| 360211 | 3/1921 | Fed. Rep. of Germany | 128/401 |
| 1179988 | 9/1985 | U.S.S.R. | 128/305 |
| 1428123 | 3/1976 | United Kingdom | 219/229 |

*Primary Examiner*—Max Hindenburg
*Attorney, Agent, or Firm*—Panitch Schwarze Jacobs & Nadel

[57] ABSTRACT

A glaucoma needle is provided which combines goniopuncture with cautery for perpetuating a fistula in the sclera of the eye. The needle comprises a hollow casing forming a point, electrically activated thermal means which generate a thermal heat band on the casing, the band extending radially from the center of the casing and connector means for attaching the thermal means to a power supply. In the method of this invention the glaucoma needle is passed through the clear cornea, across the anterior chamber to the opposite anterior chamber angle and then out at the limbus to form a goniopuncture which is cauterized by the application of heat from the thermal heat zone created by the needle.

18 Claims, 1 Drawing Sheet

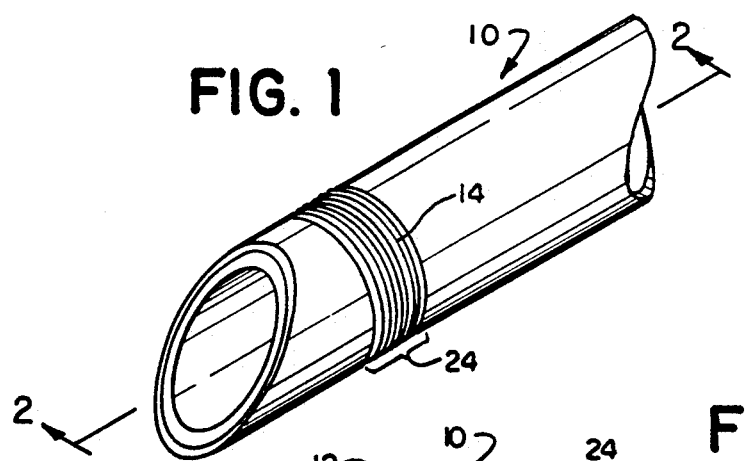
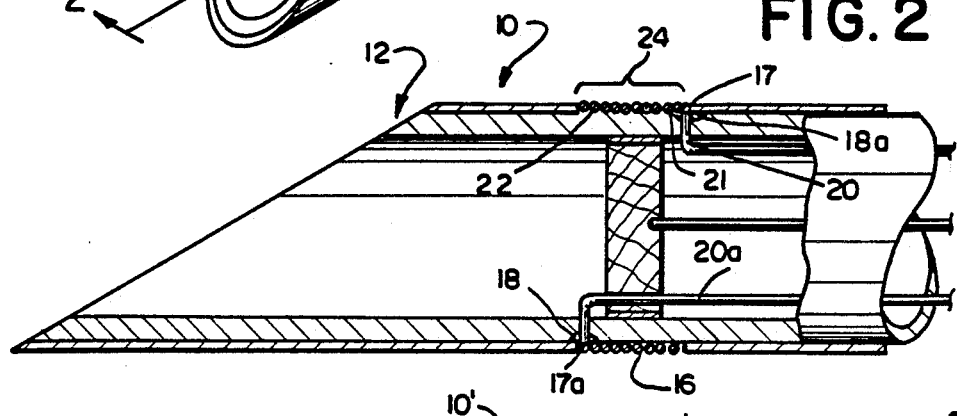
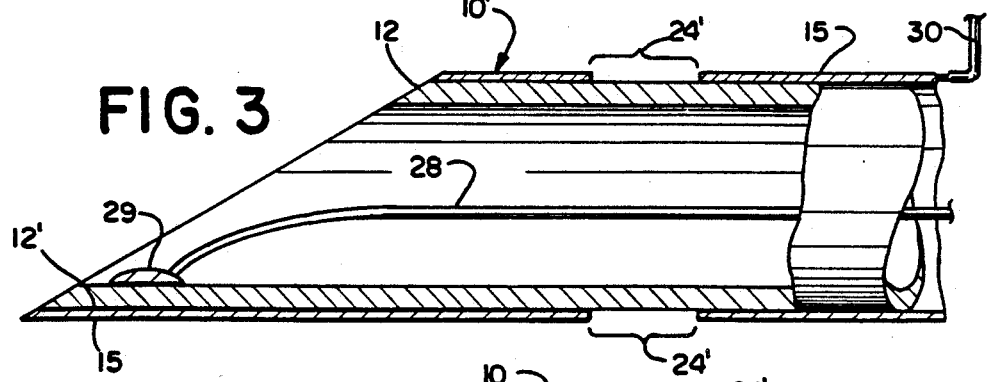
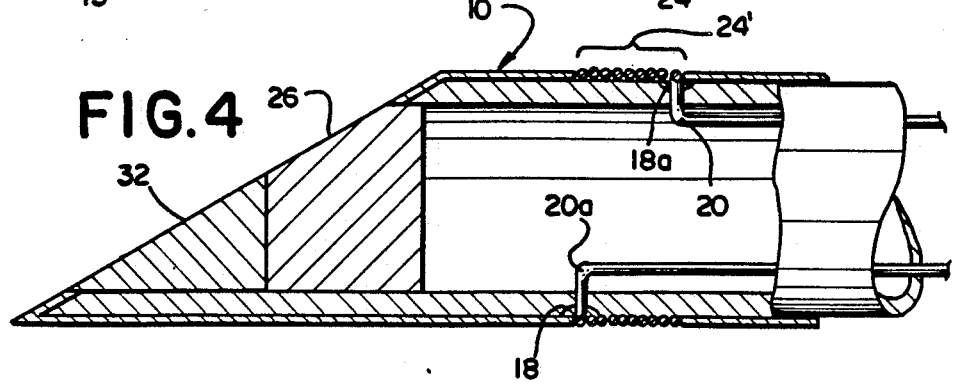

GLAUCOMA NEEDLE WITH A THERMAL HEAT BAND

BACKGROUND OF THE INVENTION

This invention is directed to a needle for glaucoma surgery. More particularly, the invention is directed to a glaucoma needle which combines the operations of goniopuncture with that of sclera cautery for perpetuating a fistula in the sclera of the eye.

Glaucoma is a condition in which the intraocular pressure is elevated to the point that the optic nerve at the back of the eye suffers damage. Glaucoma is occasionally congenital, rarely juvenile, and commonly a disease of the older patient. There are two basic methods of treating glaucoma. One method is to reduce the intraocular pressure using drugs and another is to form a permanent puncture in the sclera of the eyeball using a surgical instrument or a laser. The sclera, the white tough outer coat of the eye is composed primarily of the protein collagen. None of these treatments works all the time, even in combination.

Conventional filtration procedures that are used for most forms of glaucoma when non-surgical means of controlling the glaucoma have failed (eye drops, systemic medication, laser trabeculoplasty) include trephine, iridectomy with cautery and trabeculectomy. Cautery procedures utilize the properties of the protein collagen which primarily comprises the sclera or tough white outer coat of the eye. Collagen undergoes permanent shrinkage when exposed to the temperatures above about 80° C.

In the 1950's Dr. Harold Scheie popularized a procedure for opening the conjunctiva externally, exposing the sclera at the limbus (the edge of the cornea), and alternately heating and cutting with the blade until the anterior chamber was opened. After a fistula was thus formed, the outer tissue (conjunctiva) was reapproximated with sutures. The result was a permanent fistula between the anterior chamber of the eye and the potential space between the sclera and the relatively loose outer tissue surrounding the eye (the conjunctiva and Tenon's capsule). However, if cautery is applied too vigorously near the suture line, an inadvertent filtration bleb is produced after any ocular surgery.

A second procedure, goniopuncture, was described by Dr. Scheie in the 1950's for use in congenital or juvenile glaucoma. In this procedure a very fine knife is passed through the clear cornea, across the anterior chamber to the opposite anterior chamber angle and then out at the limbus, creating a puncture through the sclera and allowing fluid to percolate out under the conjunctiva, to form a bleb. In this operation the conjunctiva itself is not perforated by the blade. This operation frequently failed and was successful only in young people (under 30 years of age). It had been theorized that young sclera is somewhat elastic and that poking a hole in it would allow it to retract spontaneously, maintaining a fistula for the formation of a filtration bleb. In older patients, the sclera is not so elastic and goniopuncture perforations heal without producing any lasting filtration. Nevertheless, the success rate of this operation is estimated at somewhat less than 50%, even in young people.

An additional disadvantage of all such filtration procedures is that they are performed ab externo and use up a considerable amount of the available limbus. About 60° of limbus is used for any conventional filtration procedure. Since only the upper 180° is favorable for filtration surgery, one can usually place only two conventional filtration procedures without comprising results in future procedures.

It is an objective of the disclosed invention to provide an instrument which will allow an operation to combine the best features of (1) cautery (which causes collagen to contract permanently thereby perpetuating a fistula), and (2) goniopuncture (which can be performed easily and relatively non-traumatically) using only a tiny amount of limbus (perhaps 5%), thereby allowing multiple repetition above the operation, if necessary.

It is the second objective of the disclosed invention to increase the success rate of glaucoma surgery.

It is the third objective to accomplish this operation by means of a very thin knife (less than one millimeter in diameter preferably) which can be heated to a temperature adequate to cause permanent shrinkage of the sclera at the point on the knife where the limbus is traversed.

SUMMARY OF THE INVENTION

In accordance with the invention, a glaucoma needle has been devised which permits the surgeon to combine goniopuncture with cautery to cause the collagen of the sclera to contract permanently and thereby perpetuate a fistula easily and relatively atraumatically. The surgical glaucoma needle comprises an elongated needle having a sharp point at one end an forming an electrically actuated thermal means which create a thermal heat band on the surface of said needle and connector means for connecting the electrical activated thermal means to a power supply. The glaucoma needle of the preferred embodiment can be used to permanently shrink the sclera at the point(s) at which the heated portion of the needle traverses the limbus. Consistent filtration is obtained and the operation uses only a small amount of limbus (as little at 5°) thereby permitting multiple repetitions of the operation, if necessary.

In the method of the present invention, the glaucoma needle is passed through the clear cornea, across the anterior chamber to the opposite anterior chamber angle and then out at the limbus to form a goniopuncture which is simultaneously cauterized by the application of heat. The collagen of the sclera is thereby permanently contracted and a fistula is perpetuated. The method is performed easily and relatively atraumatically and uses only a small amount of limbus (as little as 5°) allowing multiple repetitions of the operation should this be necessary. The method of the invention provides a high success rate because it provides a means by which heat can be precisely controlled and applied to cause permanent shrinkage of the sclera at precisely the area that traverses the limbus. This is possible because of the unique design of the needle.

BRIEF DESCRIPTION OF THE DRAWINGS

FIG. 1 is a perspective view of the glaucoma needle of the first embodiment.

FIG. 2 is a sectional view of the first embodiment along line 2—2 FIG. 1.

FIG. 3 is a sectional view of the glaucoma needle of the second embodiment.

FIG. 4 is a sectional view of the glaucoma needle of FIG. 2 having a plugged end.

BRIEF DESCRIPTION OF THE INVENTION

The glaucoma needle of the first embodiment is described with reference to the attached figures wherein the same numbers are used to indicate like structure.

Referring to FIG. 1, the glaucoma needle 10 of the first embodiment comprises a hollow elongated casing. The hollowness of the needles allows for irrigation during surgery. Thus, with the development of visco elastic material such as sodium hyaluronate for intraocular surgery, the anterior chamber of the eye can be filled through the needle with a very viscous chemical and surgery performed at leisure with the anterior chamber being maintained even though no further irrigation or filling takes place.

As shown in FIGS. 1 and 2, the glaucoma needle 10 of the first embodiment comprises a casing 12 composed of a material such as surgical steel. The needle shown is composed of two layers of steel. The hollow casing has a groove 14 which is machined onto its outer body and which forms a band 24 having a width of 2.0 mm and extending between 1.5 to 3.5 mm from the tip. Insulated 1 mil nichrome wire 16 is wrapped around the groove cut into the outside wall of the casing 12. The nichrome wire 16 is welded 18a to the needle itself at one border 17 of the groove. It is also welded 18 at the other border 17a of the groove to insulated copper wire conductors 20, 20a which are introduced through the interior of the needle. The spot welds are made directly. The spot welded joinder of the nichrome and copper wires is coated with any desired insulating polymer such as PYRE ML. The nichrome wire is pre-coated with an insulative polymer material 21 which both insulates the wire electrically and withstands heat.

The coiled nichrome wire is then overcoated with a second layer of temperature resistant epoxy resin 22 or other suit material which will facilitate its passing through the relatively tough cornea and sclera of the eyeball without tearing the nichrome wires. The nichrome wire coil thus defines a thermal heat band 24 upon the application of electrical energy to the conductors. Electrical current is supplied from a power source (not shown) and the amount of current generated through the heating element wires can be controlled from the power source in order to control the temperature of the heating area. In addition, a timer, controlled for example, by a foot pedal, can be used to provide bursts of heat having pre-set durations.

Referring to FIG. 4, modification of the embodiment of FIG. 1 is shown. In this embodiment, the end of the needle is plugged with a steel plug 26 which is then sharpened to the sharpest point possible. This embodiment is preferably used where the implement of this invention is employed to make its own puncture. However, whenever possible, it is preferable that the puncture and counter-puncture at the limbus 180° across from the puncture be made with a knife needle to permit entrance and egress of the needle and, later, egress of the aqueous humor from the conjunctiva. A diamond or sapphire point 32 may be placed at the tip of the needle.

In an alternative preferred embodiment of the invention, illustrated in FIG. 3, the needle operates using the needle body itself to generate the thermal heat band. Needle 10' consists of a hollow steel casing 12, which is plated with gold 15 to the borders of the thermal heat band 24'. Preferably, the gold 15 is thickly plated. Although gold is preferred because it provides optimum results with the least risk of corrosion, any other suitable inert metallic or nonmetallic material that will conduct electrical current may be used instead of or in addition to gold.

The gold or other conducting material 15 may be applied to the needle of this invention in any suitable manner as desired including plating or a conventional sputtering process. In a sputtering process, the needles are supported on a suitable base and plated with gold or other coating material in a vacuum chamber which contains a small quantity of argon or other gas. The gold or other coating is given a negative charge and the needles are given a positive charge. The molecules will move at a high speed striking the gold or other coating surface.

After the desired quantity of gold or other coating material is deposited on the needle, the needle is removed from the vacuum chamber. A portion of gold coating is then removed in order to define a thermal heat band 24'. Alternatively, the tip and thermal heating band 24, can be protected during sputtering so that the gold or other heating material does not deposit on the protected areas but is applied selectively.

A wire of copper, platinum or any other suitable electrically conductive material 28 leads from a power supply (not shown) extends axially through the interior of the needle and is secured to the inner wall by a spot weld 29. A second electrical connection 30 is made to the gold plate or other suitable coating. The result is the creation of a circuit which includes the body of the needle 12'. Upon the application of electric power, the steel heats up relative to the less resistive gold. Gold is approximately 50 times less resistive than steel. This results in the creation of a heating band 24' on needle 10', upon the application of electrical power to the conductors 28, 30. The temperature is controlled in a range adequate to permanently shrink the collagen of the sclera, most preferably somewhat above 80° C. This temperature provides a very effective means for goniopuncture-cautery to perpetuate a fistula. The needle 12' may include a plug similar to the plug 26 in FIG. 4. The plugged end may have a diamond or ceramic tip 32.

The operation of the glaucoma needle of the first embodiment is described with reference to FIGS. 1,2 and 4. Initially a power supply (either AC or DC) is attached to the two conductor leads. The leads then form an electrical loop with the nichrome wire wrapped about the groove on the outer casing, which heats up when the power is turned on. The wire produces heat at a band of approximately 80° C.

In the second embodiment shown in FIG. 3, electric current is applied from the conductor 28 to the spot weld 29 on the stainless steel portion of the needle. A second conductor 30 is affixed to the gold outer coating 15. Upon the application of electric power to the first conductor, the more resistive steel heats up relative to the gold, thereby creating a heat zone on the exposed steel portion of the tube on which the gold was stripped away. Thus, due to the difference in conductivities between the two metals, the generated heat is restricted to thermal zone or band 24'.

In the method of this invention, the glaucoma needle is passed through the clear cornea, across the anterior chamber of the eye to the opposite anterior chamber at an angle and then out at the limbus to form a goniopuncture which is simultaneously cauterized by the application of heat from the thermal band. The collagen of the sclera is thereby permanently contracted and a fistula is perpetuated. The process is performed easily and relatively atraumatically and uses only a small amount of limbus (as little at 5°) allowing multiple repetitions of the operation should this be necessary. The use of the glaucoma needle has a high success rate because it provides a means by which heat can be precisely controlled and applied to cause permanent shrinkage of the sclera at precisely the area that traverses the limbus. This is possible because of the unique design of the needle of the present invention.

Although the invention has been described in considerable detail in the foregoing, it is understood that such detail is solely for the purpose of illustration and that variations may be in the invention by those skilled in the art without departing from the spirit and scope of the invention except as set forth in the claims.

What is claimed is:

1. A surgical glaucoma needle comprising:
   an elongated needle having a sharp point at one end and an outer surface extending away from the one end;
   electrically actuated thermal means extending along only a portion of the outer surface proximal the one end for creating a discrete, thermal heat band on the outer surface of the needle proximal the one end; and
   electrical connectors for connecting said electrically actuated thermal means to a power supply.

2. The surgical glaucoma needle recited in claim 1 wherein said thermal heat band occupies a region on the needle spaced from the sharp end of the needle.

3. The surgical glaucoma needle recited in claim 2 wherein the point of said needle is plugged.

4. The surgical glaucoma needle recited in claim 3 wherein the point of said needle is diamond tipped.

5. The surgical glaucoma needle recited in claim 2, wherein a remaining portion of the outer surface of the needle is substantially uniform and different from the portion defining the thermal heat band.

6. The surgical glaucoma needle recited in claim 1 wherein the needle comprises a hollow metallic casing, wherein the outer surface comprises a coating on the casing and wherein the annular region is provided by a gap in the coating exposing an annular portion of the casing.

7. The surgical glaucoma needle of claim 1 wherein the coating is formed by a metal plated to the hollow metallic casing, wherein the electrical resistance of the metal of the hollow casing is a sufficient number of times greater than the electrical resistance of the plated metal that heat generated along the outer surface of the needle by passing electric current through the needle is essentially confined to the annular region.

8. The surgical glaucoma needle of claim 7 wherein the annular portion of the hollow metallic casing exposed through the plated metal is about 2 mm. wide.

9. The surgical glaucoma needle of claim 1 wherein the needle comprises a hollow metallic casing forming the outer surface, wherein the annular region is a groove on the casing and wherein the electrically actuated thermal means comprises an electrical conductor wrapped around the casing along the groove.

10. The surgical glaucoma needle of claim 9 wherein the electrical connectors extend within the hollow casing to the wrapped electrical conductor and are electrically coupled with the wrapped electrical conductor through the metallic casing.

11. The surgical glaucoma needle of claim 10 wherein the groove and wrapped metallic conductor both extend about 2 mm. along the outer surface of the casing.

12. The surgical glaucoma needle recited in claim 1 wherein the point of said needle is plugged.

13. The surgical glaucoma needle recited in claim 12 wherein the point of said needle is diamond tipped.

14. The surgical glaucoma needle recited in claim 13 wherein the conductor is a nichrome wire.

15. The surgical glaucoma needle recited in claim 1 wherein said needle is comprised of surgical stainless steel.

16. The surgical glaucoma needle recited in claim 1 wherein the elongated needle comprises a hollow casing and the thermal means comprises an electrical conductor wrapped on the outside of the casing, said conductor defining the thermal band.

17. A method for performing glaucoma surgery which comprises the following steps:
   (a) passing the surgical glaucoma needle recited in claim 1 through the cornea at an angle of 180°, across the anterior chamber to the opposite anterior chamber angle and then out at the limbus to form a goniopuncture; and
   (b) simultaneously cauterizing the eye by the application of heat from the thermal band of said glaucoma needle to perpetuate a fistula.

18. A surgical glaucoma needle comprising:
   an elongated needle having a sharp diamond tip at one end and an outer surface extending from the one end;
   electrically actuated thermal means for creating a discrete thermal heat band along a portion of the outer surface of the needle; and
   electric connectors for connecting said electrically actuated thermal means to a power supply.

* * * * *